United States Patent [19]

Stark

[11] Patent Number: 5,368,593
[45] Date of Patent: Nov. 29, 1994

[54] DEVICES AND METHODS FOR ATTACHMENT OF SPINE FIXATION DEVICES

[76] Inventor: John G. Stark, 19390 Walden Trail, Deephaven, Minn. 55391

[21] Appl. No.: 909,602

[22] Filed: Jul. 7, 1992

[51] Int. Cl.$^5$ .............................................. A61B 17/56
[52] U.S. Cl. ........................................ 606/61; 606/72
[58] Field of Search ................................... 606/61-69, 606/70, 71, 72, 73, 74, 76, 77; 411/370, 371, 372, 373, 457

[56] References Cited

U.S. PATENT DOCUMENTS

| | | | |
|---|---|---|---|
| Re. 27,085 | 3/1971 | Weidner | 411/371 |
| 1,105,105 | 7/1914 | Sherman . | |
| 2,242,003 | 5/1941 | Lorenzo . | |
| 2,414,882 | 1/1947 | Longfellow . | |
| 2,494,229 | 1/1950 | Collison . | |
| 2,511,051 | 6/1950 | Dzus . | |
| 2,532,296 | 12/1950 | Giesen . | |
| 2,570,465 | 10/1951 | Lundholm . | |
| 2,631,584 | 3/1953 | Purificato . | |
| 3,164,418 | 1/1965 | Biesecker | 411/354 |
| 3,202,033 | 8/1965 | Weidner | 411/371 |
| 3,744,488 | 7/1973 | Cox . | |
| 3,896,504 | 7/1975 | Fischer . | |
| 4,059,102 | 11/1977 | Devas . | |
| 4,493,317 | 1/1985 | Klaue . | |
| 4,524,765 | 6/1985 | de Zbikowski . | |
| 4,564,007 | 1/1986 | Coombs et al. . | |
| 4,569,338 | 2/1986 | Edwards . | |
| 4,611,581 | 9/1986 | Steffee . | |
| 4,648,388 | 3/1987 | Steffee . | |
| 4,653,481 | 3/1987 | Howland et al. . | |
| 4,696,290 | 9/1987 | Steffee . | |
| 4,714,469 | 12/1987 | Kenna . | |
| 4,716,893 | 1/1988 | Fischer et al. . | |
| 4,793,335 | 12/1988 | Frey et al. . | |
| 4,887,595 | 12/1989 | Heinig et al. . | |
| 4,907,577 | 3/1990 | Wu . | |
| 4,913,134 | 4/1990 | Luque . | |
| 4,963,144 | 10/1990 | Huene . | |
| 4,973,333 | 11/1990 | Treharne . | |
| 5,030,220 | 7/1991 | Howland . | |
| 5,034,011 | 7/1991 | Howland . | |
| 5,084,049 | 1/1992 | Asher et al. . | |
| 5,098,434 | 3/1992 | Serbousek . | |
| 5,108,395 | 4/1992 | Laurain . | |
| 5,108,397 | 4/1992 | White . | |
| 5,108,399 | 4/1992 | Eitenmuller et al. . | |
| 5,180,393 | 1/1993 | Commarmond | 606/61 |
| 5,207,678 | 5/1993 | Harms | 606/61 |

OTHER PUBLICATIONS

Amset R-F document, entitled "Reduction-Fixation System Surgical Technique", dated 1991, Exhibit A.
"Mechanical Stability of the Pedicle Screw Fixation Systems for the Lumbar Spine", SPINE, Asian Edition, vol. 17-No. 3S, pp. S51-S54, dated Mar. 1992, Exhibit B.
"Human Lumbar Vertebrae-Quantitative Three-Dimensional Anatomy", SPINE, vol. 17-No. 3, pp. 299-306, dated Mar. 1992, Exhibit C.

Primary Examiner—Michael A. Brown
Attorney, Agent, or Firm—Merchant, Gould, Smith, Edell, Welter & Schmidt

[57] ABSTRACT

The present invention relates to apparatus and methods for attaching devices to bones. In particular, structure is provided for attaching spine fixation devices to individual vertebra. A screw is threadably attached to the vertebra, and a spacer is provided for receipt on the screw. The spacer is positioned to engage an exterior surface of the vertebra. The hardware, such as a nut, or saddle assembly, engages a second surface of the spacer. Various structure on the spacer may be provided to engage the bone surface. A conical, curved, or flat surface may be provided. One or more teeth may be provided for engaging the bone surface. A porous wafer may be used in combination with the spacer to permit bone ingrowth into the porous wafer following attachment. Porous material may also be used in connection with the spacer surface which engages the bone surface. Additional spacers may be provided to further position the hardware away from the surface of the bone. By tightening down the hardware on the second surface of the spacer, a secure attachment of the hardware and screw to the bone is provided.

13 Claims, 8 Drawing Sheets

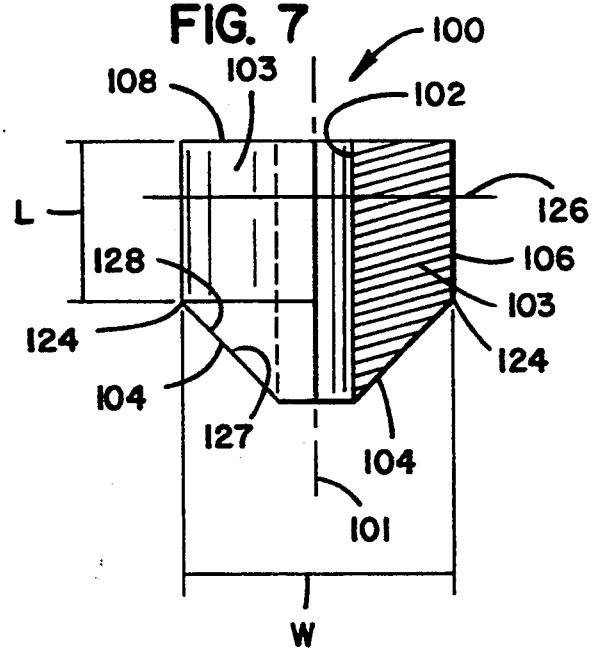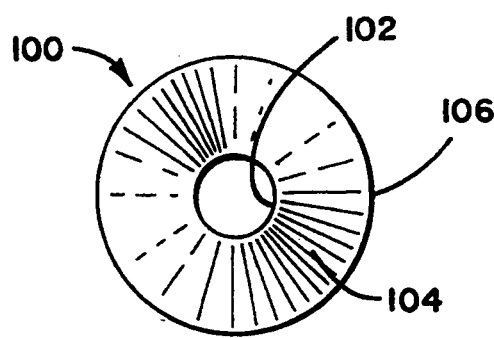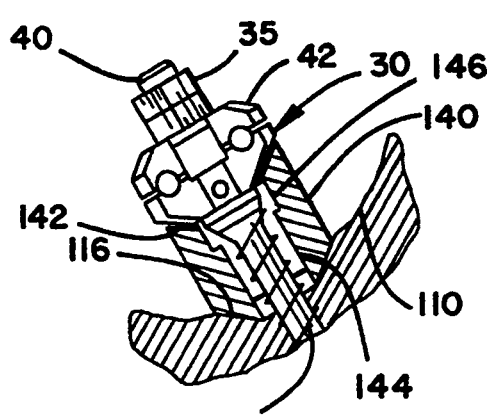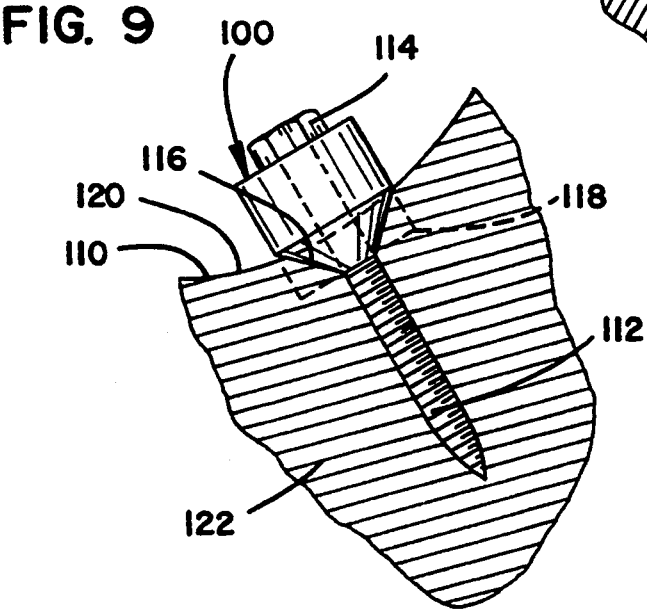

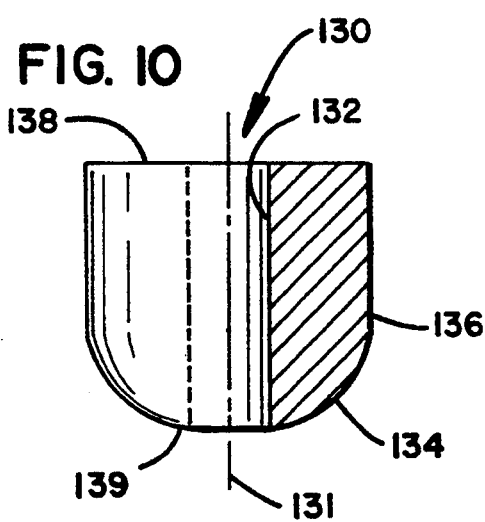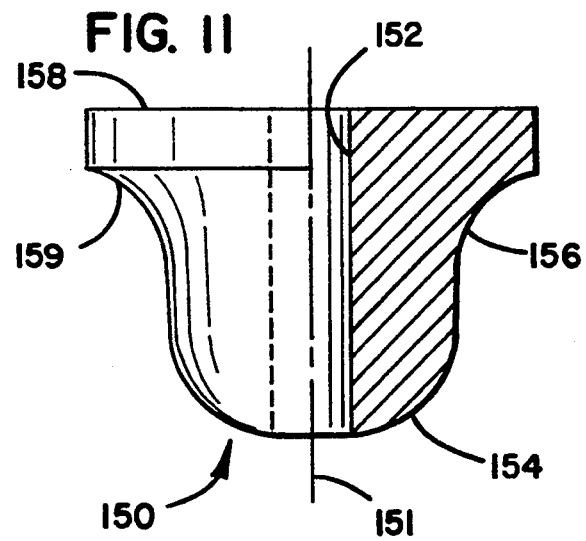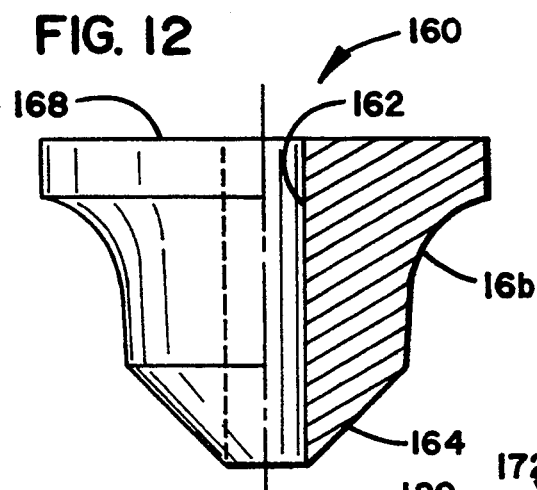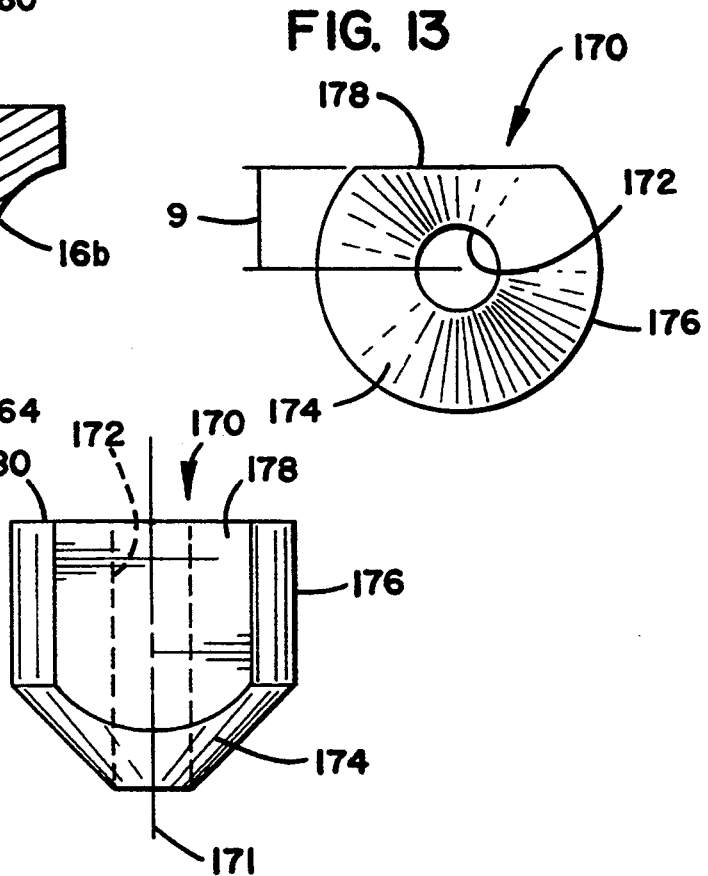

DEVICES AND METHODS FOR ATTACHMENT OF SPINE FIXATION DEVICES

FIELD OF THE INVENTION

The present invention relates generally to systems for attaching structures to bones. In particular, the present invention relates to various devices and methods for attaching spine fixation devices to portions of the spine.

BACKGROUND OF THE INVENTION

Medical procedures are known for treating various injuries or conditions where structures are attached to bones for treatment of the injury or condition. Various apparatus and methods are known for surgically treating various spinal problems wherein structures are attached to the spine. Spinal fixation procedures treat the spine by attaching devices to the spine to facilitate fixation of specified vertebrae of the spine. For example, U.S. Pat. No. 4,653,481, issued Mar. 31, 1987 to Howland et al., concerns spine fixation systems and methods. U.S. Pat. No. 5,030,220, issued Jul. 9, 1991 to Howland, concerns alternative spine fixation systems and methods. U.S. Pat. Nos. 4,653,481 and 5,030,220 are incorporated herein by reference.

U.S. Pat. Nos. 4,653,481 and 5,030,220 both relate to systems and methods which employ spine fixation devices including a plurality of clamp assemblies. Each clamp assembly is threadably attached to a vertebra of the spine. Connecting structure, such as a rod, is held by each of the clamp assemblies to connect the vertebra to facilitate fixation of the spine.

With respect to attaching spine fixation devices to the spine, a significant concern is the ability to securely attach the fixation devices to the individual vertebra. One problem encountered when attaching devices to bones such as the bony structure of vertebrae is that the vertebrae typically have irregular outer surfaces. Also, vertebrae are relatively small bones with a plurality of small and irregular projecting members, which may easily be fractured. Further, problems are presented due to the structure and composition of each vertebra. An outer portion of each vertebra usually includes relatively hard and strong cortical bone. An interior portion of each vertebra usually includes softer and weaker cancellous bone.

A need exists in the prior art for systems and methods which permit secure attachment of spine fixation devices or other devices to bones and which address at least some or all of the various concerns noted above and other concerns.

SUMMARY OF THE INVENTION

The present invention relates to spacers for use in connection with bone screws which are attached to bones. The spacer is particularly useful for attachment of screws to vertebrae. The spacer is slideably positioned on the screw shaft and securely engages the outer surface of the vertebra to which the screw is attached. A particular shape to the bone engaging surface of the spacer is provided to facilitate secure attachment of the screw to the bone wherein the screw and associated hardware can be tightened down against the bone without harming the bone. The spacer also permits the screw hardware, such as the rod clamping structure, or saddle assembly, to be positioned at a spaced apart distance from the bone surface.

The present invention relates particularly to non-cylindrically shaped spacers. If the bone surface is to be prepared for countersinking of the spacer, a non-cylindrical spacer reduces the amount of cortical bone which must be cut away. Non-cylindrical spacers also may conform better to the three-dimensional shapes of the existing bone surface. Further, non-cylindrical spacers eliminate sliding sheer action which may occur against the bone surface in the case of flat spacers.

A conical tipped spacer is an example of one non-cylindrical spacer shaped to reduce the amount of cortical bone which must be removed to provide a good seat against the bone. The conical tip is essentially a truncated cone shape due to the presence of the axial bore through the spacer to receive the screw.

Smooth curves to the spacer can be provided instead of a cone. Further, an outward flare may be provided on the spacer, whether conical- or curved-tipped. The outward flare further may help to provide a secure mounting of the screw. It is to be appreciated that in some cases sharp edges may not be desirable, since they may result in stress concentrations where bone resorption can occur. In that case, curves may be more desirable over a conical structure.

Various projections extending from the spacer may be provided to grip the bone and prevent the spacer from turning about the screw shaft. Projections such as one or more teeth may be provided to grip the bone. During attachment of the screw, the teeth are inserted axially into the bone surface.

Other projections are possible, such as curved and tilted projections which cause a twisting of the spacer as the spacer is inserted with an axial force into the bone.

A porous material may comprise the spacer or may be provided on outside surfaces of the spacer to permit bone ingrowth following attachment. A separate porous wafer may be used in between the spacer and the bone to further permit bone ingrowth and secure attachment of the screw to the bone.

In some applications, stacking of several spacers may be desirable, in connection with attachment of a single screw, to achieve the appropriate distance of the hardware away from the bone. Various shapes to the hardware surface of the spacer may be provided to engage a corresponding shape to the hardware of the bone screw apparatus, or to the second spacer added in stacked relationship. In some cases, locking structure may be provided between the bone screw apparatus and the spacer, or between stacked spacers.

BRIEF DESCRIPTION OF THE DRAWINGS

In the drawings, where like numerals refer to like components throughout the several views:

FIG. 7 illustrates a side view of a first embodiment of a spacer in accordance with the present invention, shown in partial cross-section;

FIG. 8 illustrates an end view of the spacer shown in FIG. 7;

FIG. 9 illustrates a side view of the spacer shown in FIGS. 7 and 8 used in connection with a bone screw apparatus attached to the bone;

FIG. 9A illustrates a cross-sectional side view of a modified spacer to the spacer shown in FIGS. 7–9, used in connection with a bone screw apparatus attached to the bone;

FIG. 10 illustrates a side view of a second embodiment of a spacer, shown in partial cross-section;

FIG. 11 illustrates a side view of a third embodiment of a spacer, shown in partial cross-section;

FIG. 12 illustrates a side view of a fourth embodiment of a spacer, shown in partial cross-section;

FIG. 13 illustrates an end view of a fifth embodiment of a spacer;

FIG. 14 illustrates a side view of the spacer shown in FIG. 13;

DETAILED DESCRIPTION OF THE PRIOR ART AND THE PREFERRED EMBODIMENTS

Figure 1:
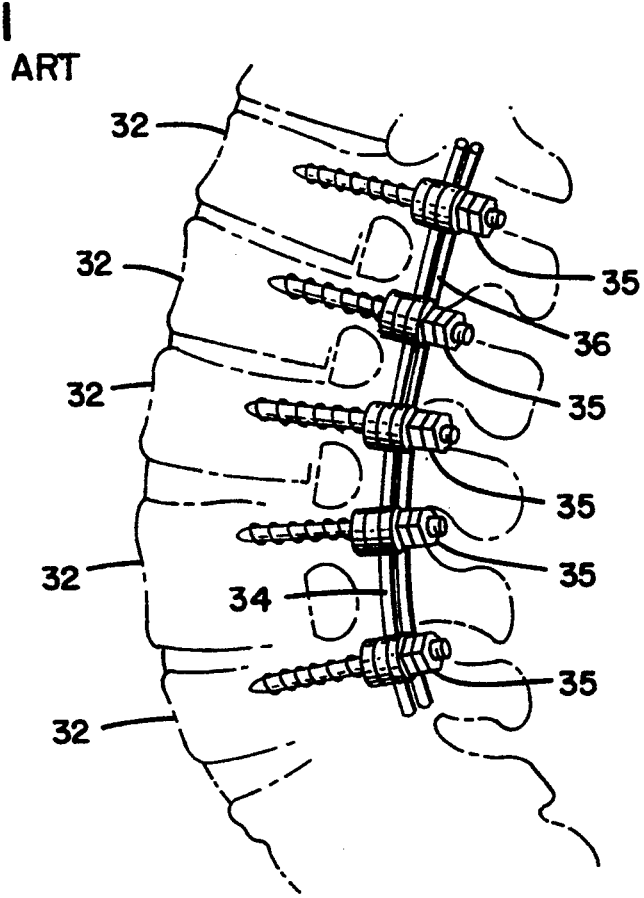
FIGS. 1 and 2 illustrate a first prior art bone screw attachment system used in connection with a spine fixation system.
Figure 2:
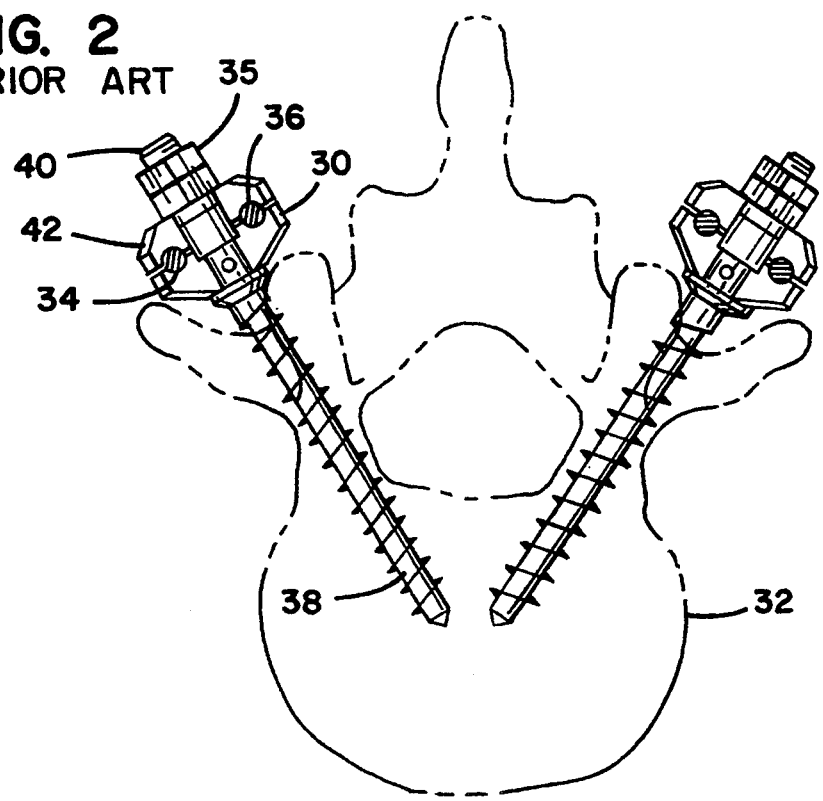

FIGS. 1 and 2 relate to prior art spine fixation systems and methods as taught by U.S. Pat. No. 4,653,481. A plurality of screw clamp assemblies 30 are attached to a plurality of vertebrae 32. Connecting rods 34, 36 between the clamp assemblies 30 connect the vertebrae to facilitate spine fixation. The clamp assemblies 30 are threadably mounted to the vertebrae.

Clamp assemblies 30 are provided with a threaded first end 38 and a threaded second end 40. The threaded first end 38 is threaded into the bony structure of the vertebra 32 of the spine. The threaded second end 40 receives the various clamping and connecting hardware associated with the spine fixation device. Screw clamp assembly 30 includes a saddle assembly 42 for mounting to rods 34, 36. The features of the systems and methods shown in FIGS. 1 and 2, and other systems and methods are discussed in greater detail in U.S. Pat. No. 4,653,481, previously incorporated by reference.

As shown in FIGS. 1 and 2, no tightening of the hardware against the outer surface of the bone is shown. Screw clamp assembly 30 is only held in place by the engagement of the threads on threaded first end 38 with the vertebra 32. In some circumstances, it may be desireable, or necessary, to provide structure to tighten the screw clamp assembly 30 against an outer surface of the vertebra.

Each vertebra typically includes a pedicle which is like a stem from which the posterior elements, such as the transverse process, the facet joints, and the dorsal process, project. The pedicle provides an access route for a screw from the posterior region of the vertebra into the vertebral body of the anterior region of the vertebra. During surgery, a screw can be introduced from the posterior region, adjacent to the facet, through the pedicle, into the vertebral body. The vertebral body is primarily soft cancellous bone, a spongy form of bone. The outer surface of the spongy bone is hard cortical, or stronger, bone. In the area of the pedicle, a layer of cortical bone typically surrounds a region of softer cancellous bone.

In many cases, it is desireable to tighten down the screw against the exterior surface of the bone in the pedicle region. Tightening down of the screw becomes difficult if bone structure interferes with the ability of the screw hardware to rest securely across the bone. In particular, the exterior surface of the natural vertebra in the pedicle region is generally three-dimensional where a number of curves meet. A flat screw head, nut or plate will typically not rest securely in this corner. Tightening the nut or plate against this three-dimensional surface will often either lever the screw hardware against the transverse process or dig into one of the posterior elements. The bone may respond to forces placed upon it by resulting in fracture. Also, the bone may respond to the high pressures by losing bone cells, causing interference with vascularity, and resulting in resorption of the bone and loosening of the screw. After a small amount of loosening of the head, nut or plate occurs, loosening of the screw and loss of fixation occurs.

Figure 3:
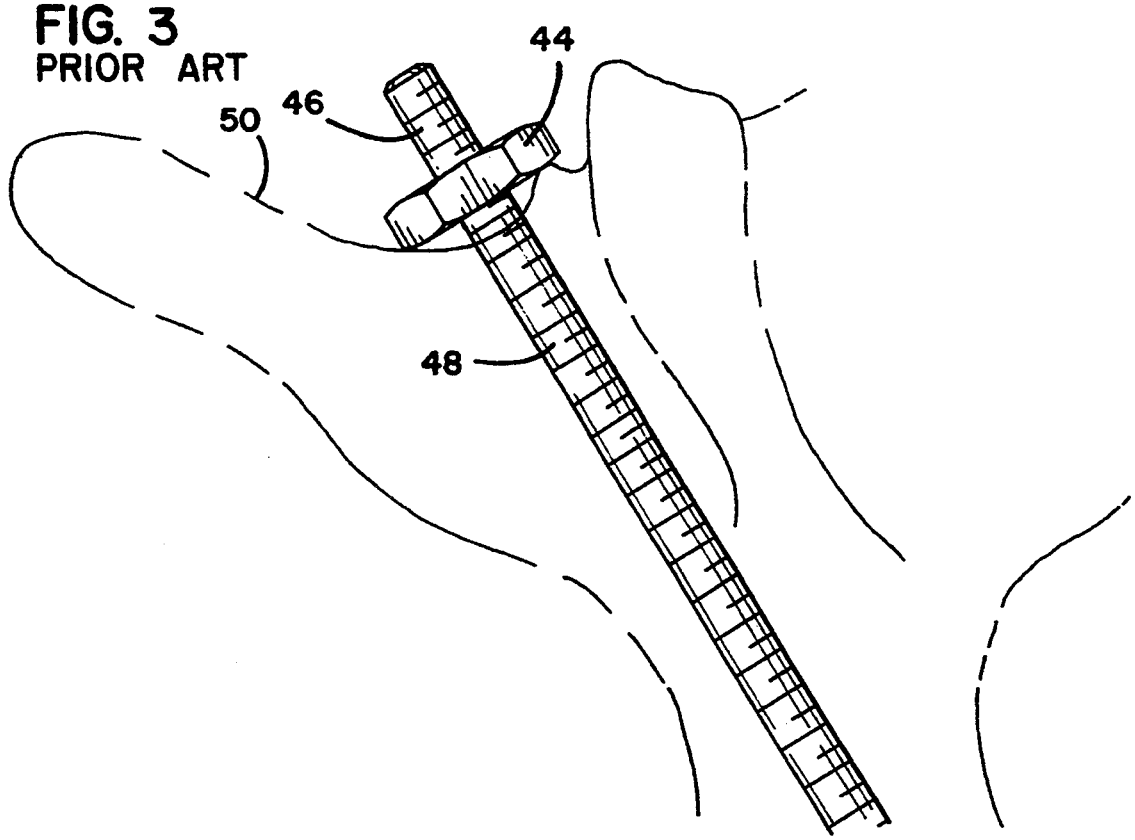
FIG. 3 illustrates a second prior art bone screw attachment system including a screw inserted into the bone and a threaded nut.
Figure 4:
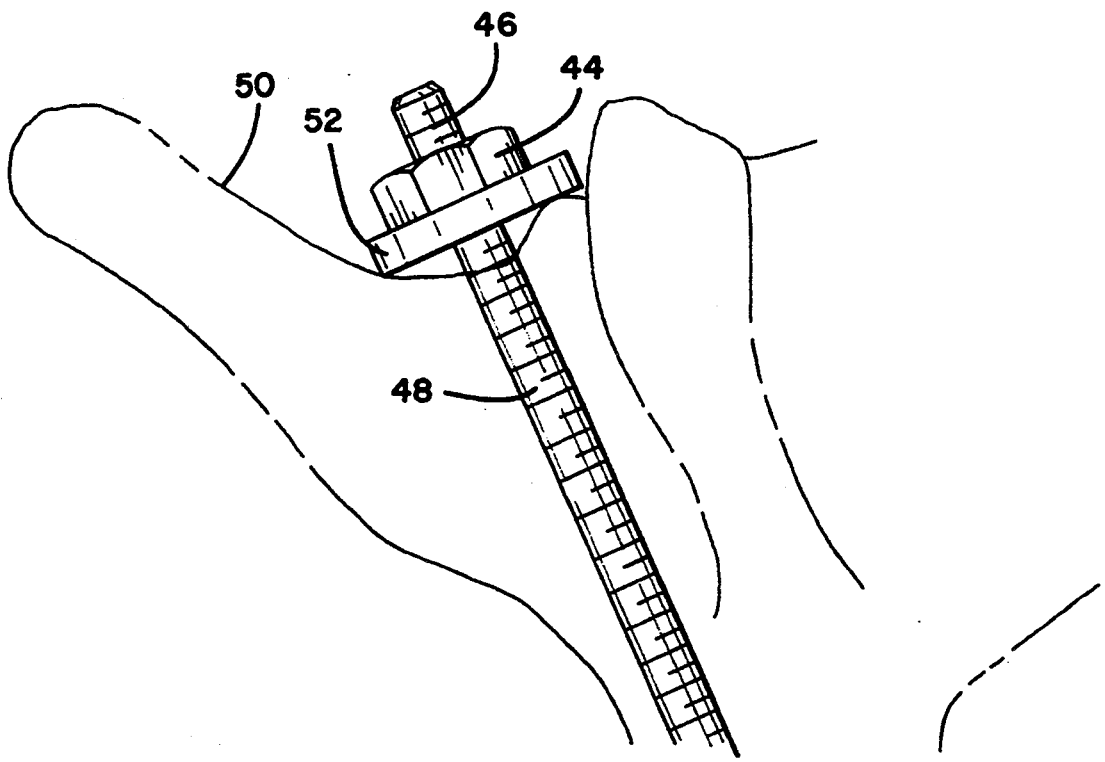
FIG. 4 illustrates a third prior art bone screw attachment system including a screw and nut like that shown in FIG. 3 and a plate positioned between the nut and the outer surface of the bone.

FIG. 3 shows a prior art arrangement involving tightening nut 44 on threaded end 46 of screw 48 directly against bone surface 50. FIG. 4 shows an alternative prior art arrangement wherein nut 44 is tightened directly against plate 52. In this arrangement plate 52 bears directly against bone surface 50. Problems arise with the systems and methods shown in FIGS. 3 and 4 due to the irregular shape of bone surface 50. The irregularities may prevent nut 44 from seating securely. The structure of FIG. 4 may result in a fracture of the bone due to the force applied by plate 52 to bone surface 50. Alternatively, bone resorption, or osteolysis, may occur where the edges of plate 52 engage bone surface 50. Fracture or resorption is likely to result in a loss of fixation.

Preparation of the bone for the screw hardware may become necessary, such as by countersinking the screw hardware, to help facilitate secure engagement of the screw hardware and the bone surface. However, a cylindrical spacer, or washer, which is countersunk into the bone necessarily weakens the bone. If too much cortical bone is removed, there may not be enough support during tightening down of the hardware. Also, the cylindrical cut-out may weaken the transverse process such that fracture occurs under very little additional force.

Figure 5:
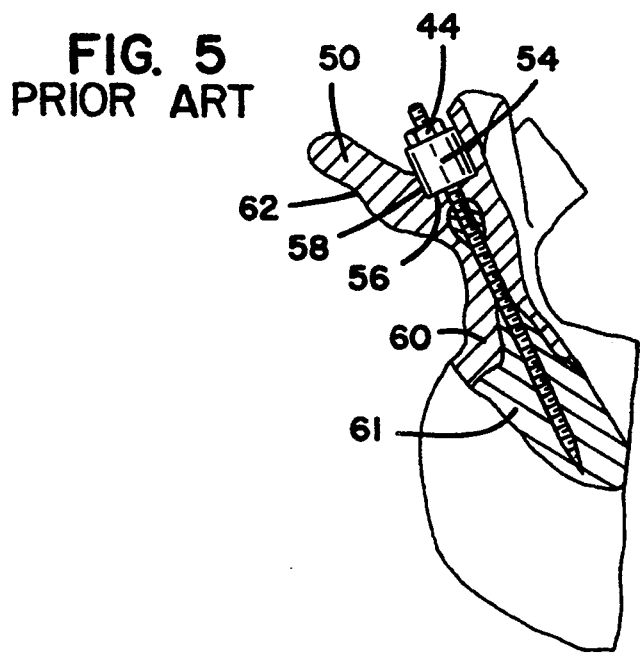
FIG. 5 illustrates a fourth prior art bone screw attachment system including a countersunk cylindrical spacer positioned between the nut and the outer surface of the bone.

FIG. 5 shows a prior art system where a spacer 54 is provided between nut 44 and bone surface 50. Spacer 54 provides a flat bottom surface 56 for engaging bone surface 50. As shown in FIG. 5, a portion of bone surface 50 may be cut away to provide a relatively smooth mating surface for flat bottom surface 56 and cylindrical side surface 58 of spacer 54. One problem with the structure of FIG. 5 is that the resistance of the cortical bone 60 is reduced or eliminated because the cut away into the bone may remove some or all of the cortical bone in this region, leaving only cancellous bone 61 to support spacer 54. Secondly, by cutting into the bone in this manner, the transverse process 62 may be weakened, causing it to be susceptible to fracture. Alternatively, the flat surface 56 of spacer 54 may not prevent vertical shear in the case when no cut away is provided.

Figure 6:
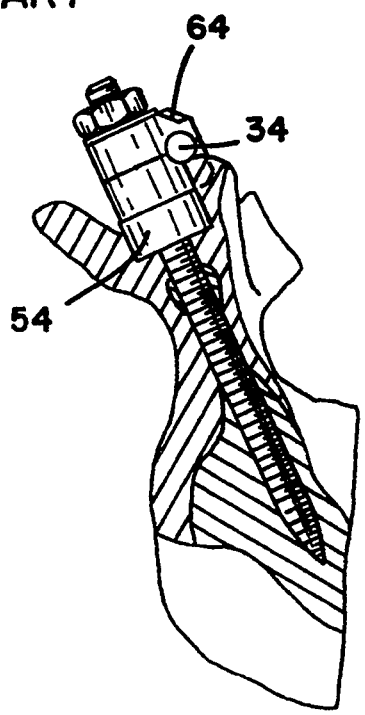
FIG. 6 illustrates a fifth prior art bone screw attachment system including a screw, a nut, a cylindrical spacer, and spine fixation hardware positioned between the nut and the cylindrical spacer.

FIG. 6 shows an alternative saddle 64 for attaching to connecting rod 34. The structure shown in FIG. 6 and other systems and methods are discussed in greater detail in U.S. Pat. No. 5,030,220, previously incorporated by reference. A cylindrical spacer 54 is shown used in connection with saddle 64.

The present invention is shown in FIGS. 7–27. Referring now to FIGS. 7 and 8, a first embodiment of a spacer 100 is shown. Spacer 100 may also be referred to as a conical spacer. Spacer 100 includes a body 103 having an axial bore 102 sized to receive a screw. The axial bore is sized sufficiently to permit the free passage of the screw through the axial bore such that any twisting or rotation of the screw about the longitudinal axis of the screw is not transmitted to the spacer 100. Spacer 100 includes a conical portion 104 which forms a first outer surface of the spacer. Conical portion is in the shape of a truncated cone. A hardware surface 108 is at an opposite end of spacer 100 to conical portion 104. A cylindrical surface portion or outer surface 106 connects conical portion 104 to hardware portion 108.

Axial bore 102 defines a bore axis 101 which is generally the same as the longitudinal axis of the screw when the screw is positioned within the axial bore. The body 103 has a circumferential plane 126 perpendicular to the bore axis 101. The conical portion defines an outer portion adjacent to the cylindrical portion, or outer surface 106, wherein a distance from a point on the outer portion of the conical portion 104 to a point on the circumferential plane 126 parallel to the bore axis 101 decreases as the point on the outer portion becomes further removed from the bore axis. In FIG. 7, point 127 is further from plane 126 than point 128. This configuration creates recessed corners on spacer 100 which create advantageous results.

A preferred hardware surface 108 is perpendicular to the axis 101. However, other shapes, such as curves, conical portions, or other shapes, are possible to mate appropriately with the corresponding screw hardware. In some instances, stacking of spacers is desired. In those instances, hardware surface 108 could be provided with any of a variety of reciprocal mating surfaces to mate with the second spacer.

Spacer 100 has a length L measured parallel to the longitudinal axis 101. Spacer 100 further has a width W measured perpendicular to the longitudinal axis 101. At circumference region 124, spacer 100 has the greatest width W at the shortest length L in the area of outer portion 104. Moreover, the outer portion 104 faces in a non-perpendicular and non-parallel direction to axis 101. Outer portion 104 faces in a direction having a component facing parallel to axis 101 and also a component facing perpendicular to axis 101.

Referring now to FIG. 9, conical spacer 100 is shown in use. Bone 110 includes a bone surface 120 and a bone interior 122. Screw 112 is threaded into bone interior 122. Spacer 100 is positioned on screw 112. Nut 114 is tightened down on spacer 100. Nut 114 may be a separate piece from screw 112, or it may be a head formed integrally on an end of screw 112. Nut 114 acts as a stop to prevent further insertion of the screw into the bone. When the nut is separately threaded onto screw 112, nut 114 may be tightened down against the bone once screw 112 is threaded into the bone. The act of tightening nut 114 down against spacer 100 causes a force to be exerted on the screw threads and the bone helping to secure the screw. Better attachment is screw 112 to bone 110 occurs when nut 114 is tightened down than when the screw hardware is left suspended in space disposed away from the bone, where only the screw threads hold the screw in place. Compressive forces are developed in the bone between the region engaged by the threads and the region engaged by the spacer. In some instances, screw 112 may include an opposing second end with different threads than threads on end 112 for threadably engaging nut 114.

As shown in FIG. 9, the bone has been prepared by forming a cutout 116. Cutout 116 has a reverse shape to the conical portion 104. As shown in FIG. 9 in dashed lines, a non-cutout region 118 is illustrated to show the extra bone which must be removed to adequately seat a cylindrical spacer of the type shown in FIGS. 5 and 6. This bone mass 118 remains if conical spacer 100 is used, creating a stronger and more secure attachment of screw 112.

The three-dimensional anatomy of the interior of the bone in the pedicle region is believed to be amenable to a conically-shaped spacer. The intercepting cortices of this complex area results in a somewhat star-shaped cortical buttress, against which the spacer can sit. Additionally, less bone must be removed to countersink the spacer, reducing the risk of fracture of the transverse process and creating a greater likelihood that the screw hardware will not sink into the bone since more cortical bone will likely be present than if a cylindrical spacer were used.

Referring now to FIG. 9A, a modified spacer 140 is shown. Spacer 140 has a first conical portion 144 and a second conical portion 142. First conical portion 144 engages the conically shaped cutout 116 in bone 110. Second conical portion 142 engages saddle assembly 42, like that shown in FIGS. 1 and 2. FIG. 9A is an example of the spacer 140 being shaped to cooperate with a particular shape on the spine fixation hardware. FIG. 9A is also an example of one of a variety of types of spine fixation hardware which can be used in connection with spacers 100, 140.

Various locking structures between the spacer 140 and saddle assembly 42 may be provided to limit relative rotational movement about the longitudinal axis when the saddle assembly is tightened down against the spacer. Such structure may take a variety of forms including reciprocal protrusions/recesses with rounded and/or sharp edges. Alternatively, or in addition to, sandpaper-like or steel wool-like mating surfaces can be provided to limit rotational movement due to frictional forces acting between the surfaces under the compressive forces when the saddle assembly is tightened down.

As shown in FIG. 9A, spacer 140 is provided with different diametered portions 146 and 148 for the axial bore. Such different shapes are provided to accommodate and cooperate with the structure on the screw shaft 148 of the spine fixation hardware.

Referring now to FIG. 10, a second embodiment of a spacer 130 is shown. Spacer 130 may also be referred to as a bullet-shaped spacer. Spacer 130 includes an axial bore 132 for receiving a screw. Spacer 130 includes a curved portion 134, on a tip of spacer 130. Curved portion 134 forms a first surface of spacer 134 for engaging the external surface bone 120 as shown in FIG. 9. Curved portion 134 may resemble a parabola. The bone cutout region is sized and shaped appropriately to receive curved portion 134. Adjacent the region where the curved portion 134 intersects the axial bore, such as area 139, the direction faced by the curved portion 134 is nearly or exactly facing in the same direction as the longitudinal axis. Curved portion 134 curves toward hardware surface 138. In between hardware surface 138 and curved portion 134 is a cylindrical portion 136.

Referring now to FIG. 11, a third embodiment of a spacer 150 is shown. Spacer 150 may also be referred to as a curved-flared spacer. Spacer 150 includes an axial bore 152. Spacer 150 includes a first curved portion 154 shaped similarly to curved portion 134 of spacer 130. Instead of a cylindrical portion 136, spacer 150 includes a second curved portion 156 which flares outwardly away from the longitudinal axis as the outer surface extends from the tip toward hardware surface 158. The flared portion may resemble a hyperbola. At the second curved portion 156, bone compression also occurs where curved portion 156 faces almost or completely in the same direction as axis 162, such as region 159.

Referring now to FIG. 12, a fourth embodiment of a spacer 160 is shown. Spacer 160 may also be referred to as a conical-flared spacer. An axial bore 162 extends from a tip to a hardware surface 168. A conical surface 164 similar to the conical surface shown in spacer 100 of FIGS. 7 and 8 is provided on spacer 160. A flared or curved portion 166 is provided between hardware surface 168 and conical portion 164 like that shown in FIG. 11 for spacer 150.

Referring now to FIGS. 13 and 14, an asymmetric spacer 170 is shown. Asymmetric spacer 170 includes an axial bore 172. An asymmetric portion 178 is provided to permit usage in situations where bony structure exists that cannot be easily removed. Asymmetric portion 178 permits usage in tight areas where spacers like those shown in FIGS. 7-12 may not easily fit. Asymmetric spacer 170 includes a conical portion 174 shaped similarly to the conical portion 104 of spacer 100, except for the asymmetric portion 178. Asymmetric portion 178 is planar in the embodiment shown. A cylindrical portion 176 is further provided similarly to the cylindrical portion 106 of spacer 100, except for asymmetric portion 178. Hardware surface 180 is provided to engage the nut or other hardware interconnected to the screw, as shown in FIG. 9.

Distance "a" shown in FIG. 13 may be varied as desired depending on the particular anatomy of the patient relative to the desired path of the screw into the patient's vertebra.

Figure 15:
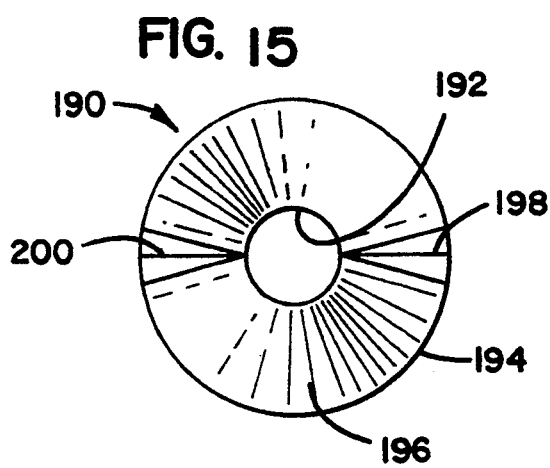
FIG. 15 illustrates an end view of a sixth embodiment of a spacer.
Figure 16:
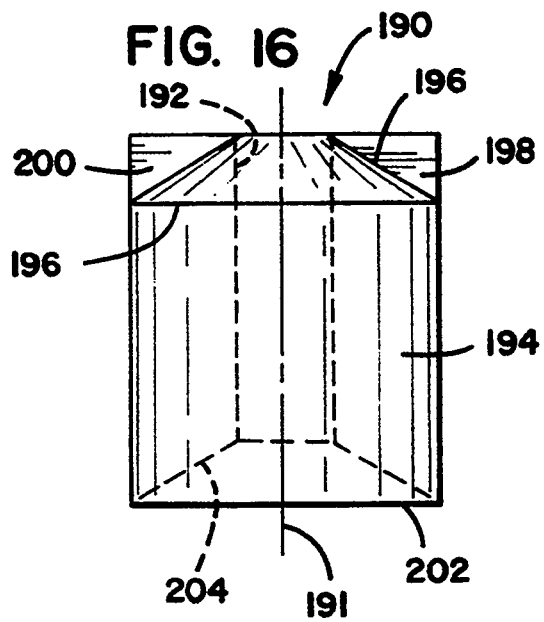
FIG. 16 illustrates a side view of the spacer shown in FIG. 15.
Figure 17:
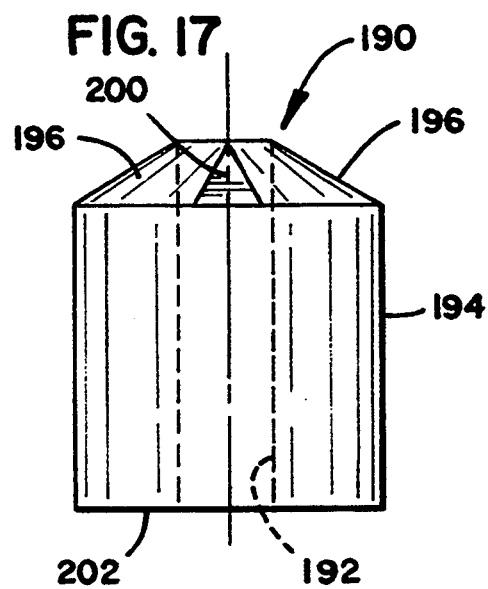
FIG. 17 illustrates another side view of the spacer shown in FIG. 15.

Referring now to FIGS. 15-17, a sixth embodiment of a spacer 190 is shown. Spacer 190 includes an axial bore 192 for receipt of a screw. Spacer 190 includes a cylindrical portion 194. A conical portion 196 permits reduced cutouts of the bone required to form a secure seat against the bony surface. However, spacer 190 may or may not be countersunk into the bone. Extending from conical portion 196 are teeth 198, 200 for engaging the bony surface. During use, spacer 190 is inserted axially toward the bone. Teeth 198, 200 dig into the bone and help provide a further secure attachment of the hardware to the bone. Hardware surface 202 permits tightening down of a nut or other hardware against the spacer. Hardware surface 202 has a conically shaped portion 204, like spacer 140 shown in FIG. 9A.

Figure 18:
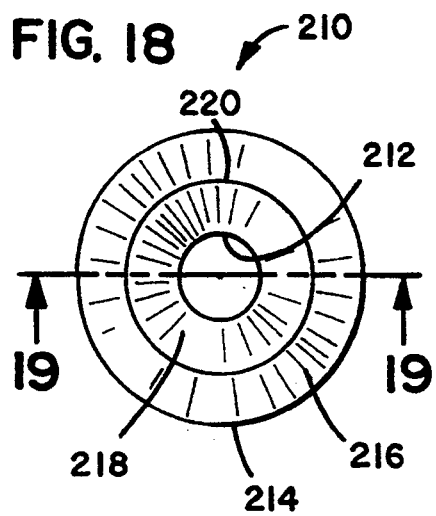
FIG. 18 illustrates an end view of a seventh embodiment of a spacer.
Figure 19:
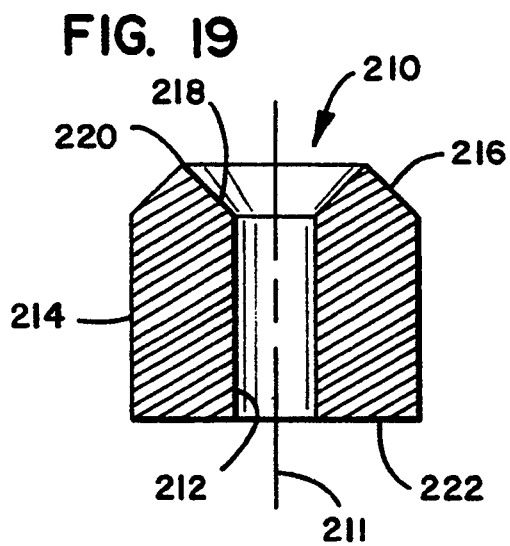
FIG. 19 illustrates a cross-sectional side view of the spacer shown in FIG. 18, along lines 19—19.
Figure 20:
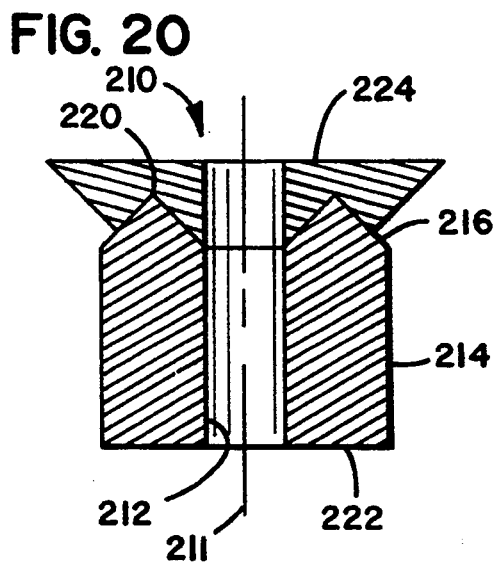
FIG. 20 illustrates the spacer shown in FIGS. 18 and 19 used in combination with a porous wafer.

Referring now to FIGS. 18-20, a seventh embodiment of a spacer 210. Spacer 210 may be referred to as a double-cone spacer. Spacer 210 includes an axial bore 212 for receiving a screw. The bone-engaging region of spacer 210 includes a first conical portion 216 and a second conical portion 218, which intersect at tip 220. First conical portion 216 diverges from tip 220 away from the longitudinal axis. Second conical portion 218 converges toward the longitudinal axis from tip 220. A hardware surface 222 permits secure mounting of the nut or other hardware adjacent spacer 210.

As shown in FIG. 20, a wafer 224 may be positioned adjacent spacer 210 such that wafer 224 engages the bone surface during attachment of the screw and spacer to the bone. Wafer 224 may be made from a variety of biologically acceptable porous materials, including porous titanium. Porous titanium permits bone to grow in the interstices between the titanium. This may produce a more secure attachment of the screw to the bone.

Figure 21:
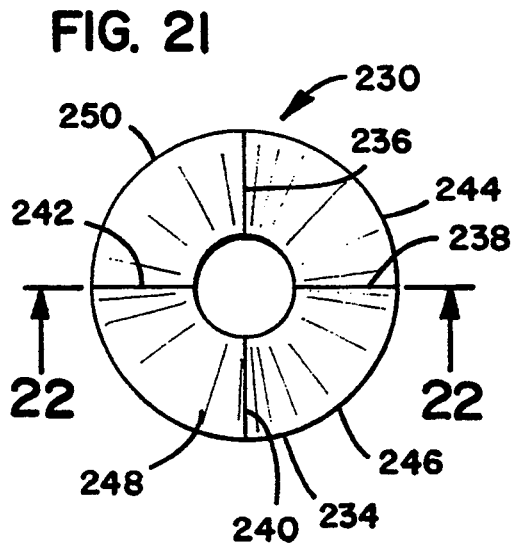
FIG. 21 illustrates an end view of an eighth embodiment of a spacer.
Figure 22:
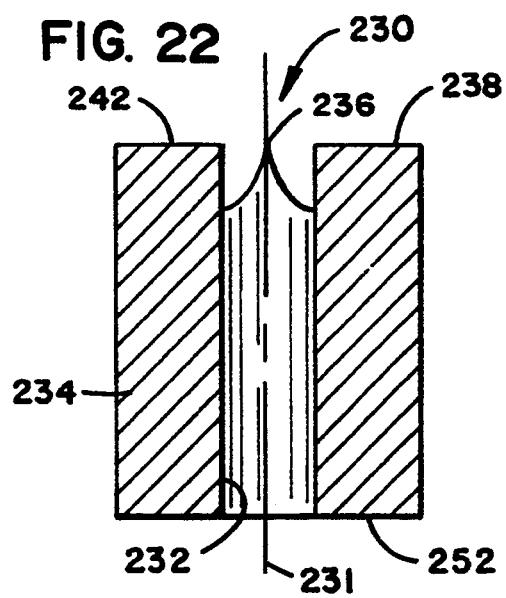
FIG. 22 illustrates a cross-sectional side view of the spacer shown in FIG. 21, along lines 22—22.
Figure 23:
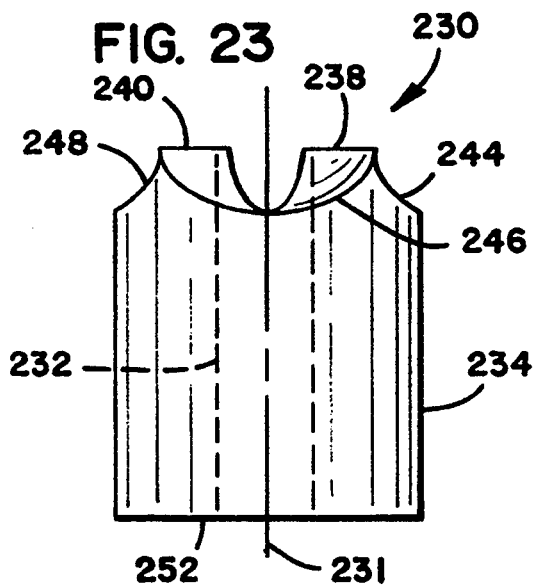
FIG. 23 illustrates a different side view of the spacer shown in FIGS. 21 and 22.

Referring now to FIGS. 21-23, an eighth embodiment of a spacer 230 is shown. Spacer 230 may also be referred to as a curved-toothed spacer. Spacer 230 includes a cylindrical portion 234 and an axial bore 232. A plurality of teeth 236, 238, 240, 242 projects from a first end of the spacer 230 for engaging and digging into the bone surface. Between teeth 236, 238, 240, 242 are curved portions 244, 246, 248, 250. Spacer 230 includes a hardware surface 252.

Figure 24:
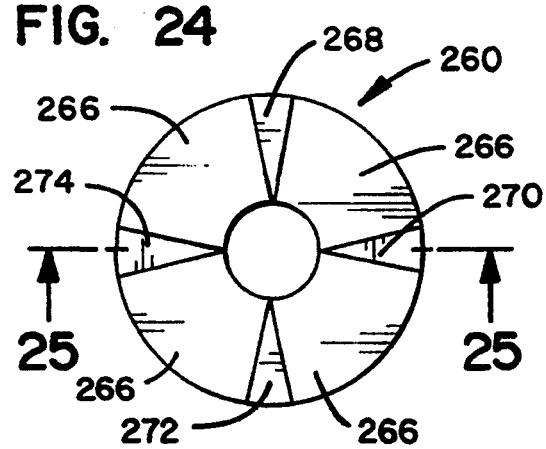
FIG. 24 illustrates an end view of a ninth embodiment of a spacer.
Figure 25:
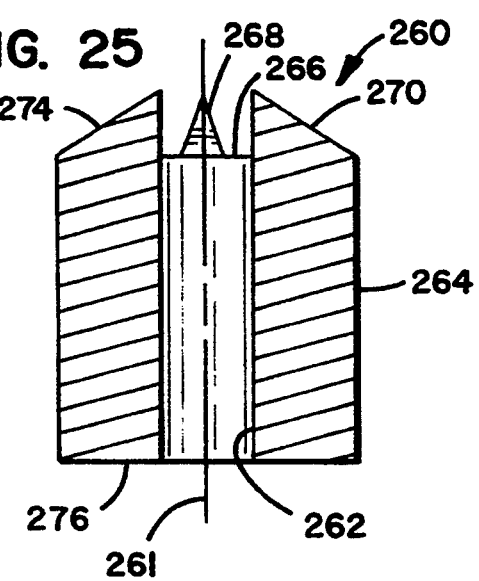
FIG. 25 illustrates a cross-sectional side view of the spacer shown in FIG. 24 along lines 25—25.

Referring now to FIGS. 24 and 25, a ninth embodiment of a spacer 260 is shown. Spacer 260 may also be referred to a straight-toothed spacer. Spacer 260 includes an axial bore 262 for receiving a screw. Spacer 260 includes a cylindrical portion 264 extending from a flat-based portion 266 to a hardware surface 276. A plurality of teeth 268, 270, 272, 274 project from base portion 266.

Figure 26:
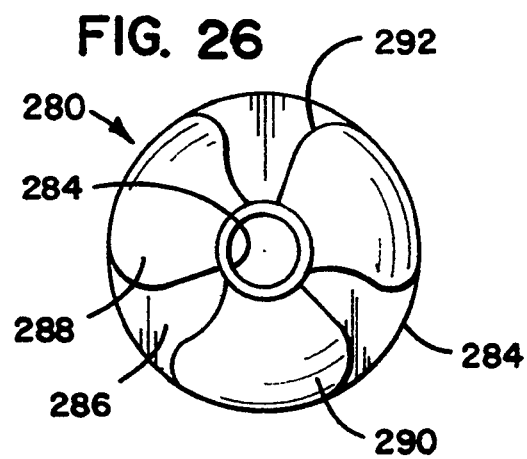
FIG. 26 illustrates an end view of a tenth embodiment of a spacer.
Figure 27:
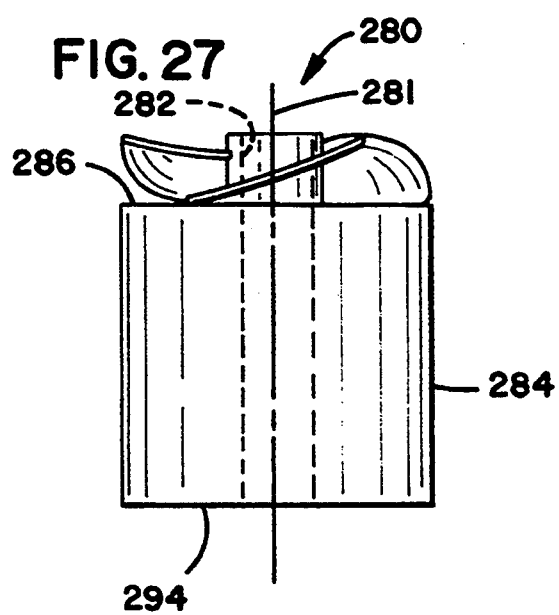
FIG. 27 illustrates a side view of the spacer shown in FIG. 26.

Referring now to FIGS. 26 and 27, a tenth embodiment of spacer 280 is shown. Spacer 280 may also be referred to as a twist spacer. Spacer 280 includes an axial bore 282. A cylindrical portion 284 extends from base surface 286 to hardware surface 294. A plurality of curved and tilted projections 288, 290, 292 extends from base surface 286. As spacer 280 is pressed into the bone in a direction of the longitudinal axis, curved projections 288, 290, 292 cause turning or twisting of spacer 280 about the longitudinal axis. This helps promote more secure mounting of the spacer and screw to the bone.

The spacers described above can be made from a variety of materials such as biologically acceptable stainless steel, titanium, or ceramics. Porous material which permits bone ingrowth may be used. The spacers can be made completely of the porous material, or the spacers can be made to include just all of the surfaces or selected surfaces or regions of porous material. Bone ingrowth may help create a more secure mounting of the spacer to the bone. Porous material may be used on the same spacer where interlocking structure is provided between the screw and the spacer to further create a more secure mounting arrangement.

In some cases it may be desireable to remove the spine fixation device or other structure from the patient. Bone ingrowth into the spacer or screw hardware may not permit easy removal of the hardware unless the bone ingrowth is appropriately controlled.

It is to be appreciated that the various spacers described above can be used with a corresponding cutout in the bone or by merely resting on the exterior surface of the bone without any bone preparation.

The invention is not to be construed as to be limited to the specific embodiments shown in the drawings, but is to be limited only by the broad general meanings of the following claims.

What is claimed is:

1. A spacer for use with a bone screw apparatus attached to a bone, the bone having an external surface, the bone screw apparatus including a shaft defining a longitudinal axis and having a first threaded end and an opposite second end having a stop interconnected to the second end, said spacer comprising:
    a tapered first surface for engaging the external surface of the bone;
    a second surface spaced apart from said tapered first surface for engaging the stop; and
    a body disposed between said tapered first surface and said second surface, said body having an outer surface extending from said tapered first surface to said second surface, and an inner surface defining an axial bore extending from said tapered first surface to said second surface, said axial bore sized to slidably receive the shaft of the bone screw apparatus in a direction of the longitudinal axis, wherein said spacer is positioned between the stop of the bone screw apparatus and the external surface of the bone, wherein said body spaces the stop at a spaced apart distance from the external surface of the bone in a direction of said longitudinal axis, said axial bore having a bore axis generally the same as the longitudinal axis when the bone screw apparatus is positioned within said axial bore;
    said body having a circumferential plane perpendicular to said bore axis, said tapered first surface having an outer portion adjacent to said outer surface, wherein a distance from a point on said outer portion of said tapered first surface to a point on said circumferential plane parallel to said bore axis decreases as said point on said outer portion becomes further removed from said bore axis;
    said outer surface of said body spaced from said bore axis at least in an equal to manner wherein a first portion of said outer surface of said body is spaced from said bore axis a distance equal to or greater than a distance of a previous portion of said outer surface in a direction of travel along said outer surface from said tapered first surface to said second surface;
    said outer surface of said body including cylindrical portion contiguous with said second surface.

2. The spacer of claim 1, wherein said spacer includes a tip and said outer portion of said tapered first surface includes a conical portion diverging from said tip away from said bore axis in a direction toward said second surface.

3. The spacer of claim 2, wherein said cylindrical portion connects said conical portion to said second surface.

4. The spacer of claim 2, further comprising a tooth projecting from said conical portion in a direction of the longitudinal axis.

5. The spacer of claim 2, wherein said outer surface of said body includes a flared portion extending in an increasing manner from said bore axis from a region adjacent to said conical portion in a direction toward said cylindrical portion.

6. The spacer of claim 2, wherein said spacer is asymmetrical about said bore axis.

7. The spacer of claim 6, wherein said outer surface of said body includes a planar portion extending in a direction parallel to said bore axis and intersecting with said conical portion.

8. The spacer of claim 2, wherein said inner surface of said body includes a second conical portion which extends from said tip and converges toward said bore axis in a direction toward said second surface.

9. The spacer of claim 1, wherein said tapered first surface includes a porous region to permit bone growth from the bone into said porous region.

10. The space of claim 1, wherein said spacer includes a tip and said outer portion of said tapered first surface includes a curved portion diverging from said tip away from said bore axis in a direction toward said second surface.

11. The spacer of claim 10, wherein said cylindrical portion connects said curved portion to said second surface.

12. The spacer of claim 10, wherein said outer surface of said body includes a flared portion extending in an increasing manner from said bore axis from a region adjacent to said curved portion in a direction toward said cylindrical portion.

13. A method of securing a screw to a vertebra, said method comprising the steps of:
    contouring the vertebra to include a recess with a conically-shaped portion;
    threadably attaching a screw to the vertebra, wherein said screw passes through said recess;
    slidably positioning on said screw an annular spacer with a conical portion to mate with said conically-shaped portion;
    providing stop means interconnected to said screw to engage said spacer; and
    tightening said stop means against said spacer wherein said spacer engages said annular recess in said bone.

* * * * *